US 6,998,637 B2
(12) United States Patent
Luyken et al.

(10) Patent No.: US 6,998,637 B2
(45) Date of Patent: Feb. 14, 2006

(54) CIRCUIT ELEMENT HAVING A FIRST LAYER COMPOSED OF AN ELECTRICALLY INSULATING SUBSTRATE MATERIAL, A METHOD FOR PRODUCING A CIRCUIT ELEMENT, BISPYRIDINIUM COMPOUNDS AND THEIR USE IN CIRCUIT ELEMENTS

(75) Inventors: R. Johannes Luyken, München (DE); Markus Seitz, München (DE); Jon Preece, Birmingham (GB); Werner Weber, München (DE); Günter Schmid, Hemhofen (DE)

(73) Assignee: Infineon Technologies AG, (DE)

( * ) Notice: Subject to any disclaimer, the term of this patent is extended or adjusted under 35 U.S.C. 154(b) by 371 days.

(21) Appl. No.: 10/600,750

(22) Filed: Jun. 19, 2003
(Under 37 CFR 1.47)

(65) Prior Publication Data

US 2005/0099209 A1    May 12, 2005

(30) Foreign Application Priority Data

Jun. 21, 2002    (DE)    ................ 102 27 850

(51) Int. Cl.
*H01L 35/24*    (2006.01)
(52) U.S. Cl. .................. 257/40; 365/151; 365/153
(58) Field of Classification Search ................ 365/151, 365/153; 257/72, E29.272; 327/10; 438/200
See application file for complete search history.

(56) References Cited

U.S. PATENT DOCUMENTS 6,198,655 B1 * 3/2001 Heath et al. ................. 365/151

FOREIGN PATENT DOCUMENTS

| DE | 42 17 588 | 12/1993 |
|---|---|---|
| DE | 198 01 638 | 7/1999 |
| DE | 100 23 765 | 11/2001 |
| DE | 101 26 578 | 12/2002 |
| DE | 101 32 640 | 1/2003 |
| JP | 56118002 | 9/1981 |
| JP | 57014507 | 1/1982 |

OTHER PUBLICATIONS

C.P. Collier et al., Electronically configurable molecular-based logic gates, Science, vol. 285, S. 391-394, 1999.
C.P. Collier et al., A [2] Catenane-based solid state electronically reconfigurable switch, Science, vol. 289, pp. 1172-1175, 2000.
D.I. Gittins et al., A nonometre-scale electronic switch consisting of a metal cluster and redox-addressable groups, Nature, vol. 408, pp. 67-69, 2000.

(Continued)

*Primary Examiner*—Mai-Huong Tran
(74) *Attorney, Agent, or Firm*—Altera Law Group, LLC; Jeffrey R. Stone

(57) ABSTRACT

The circuit element has a first layer composed of an electrically insulating substrate material and a first electrically conductive material which is in the form of at least one discrete area such that it is embedded in the substrate material and/or is applied to the substrate material. Furthermore, it has a second layer having a second electrically conductive material, and a monomolecular layer composed of redox-active bispyridinium molecules, which is arranged between the first layer and the second layer. The bispyridinium molecules are immobilized on the electrically conductive material which is in the form of at least one discrete area, and make electrical contact with the second electrical material of the second layer. Furthermore, electrically inert molecules are immobilized on the first layer, which molecules form a matrix which surrounds the at least one discrete area with the monomolecular layer composed of bispyridinium molecules.

29 Claims, 5 Drawing Sheets

OTHER PUBLICATIONS

Kawashima et al., The synthesis and properties of a methylviologen analogue, Tetrahedron Letters, vol. 25, Nr. 25, pp. 1585-1586, 1984.

A.J. Blacker et al., Molecular Anion Binding and Substrate Photoxidation in Visible Light by 2, 7-Diazapyrenium Cations, Helvetica Chemica Acta, vol. 70, pp. 1-12, 1987.

R. Bauer et al., Synthesis and electrochemical properties of some new bypuridinium and related compounds, Z Naturforsch., B: Chem. Sci. 43(4), pp. 475-482, 1988.

J. March, Advanced Organic Chemistry, 3. Auflage (Wiley, New York, 1985), p. 597H.

P. Stehle et al., Isotachophoresis of quarternary 4,4'-Bipyridylium Salts—Analytical control of synthesis and purification procedures, J. Chromatogr. 449(1), 299-3-5, 1988.

H.C. Delong & D.A. Buttry, Ionic Interaktions play a major role in determining the electrochemical behavior of self-assembling viologen monolayers, Langmuir, 6, pp. 1319-1322, 1990.

X. Tang et al., A vibrational spektroskopic study of the structure or electroactive self-assembled monolayers ofviologen derivatives; Langmuir, 10, pp. 2235-2240, 1994.

H.C. Delong & Bettry, Environmental effects on redox potential of viologen groups in electroactive self-assembling viologen monolayers, Langmuir, 8, pp. 2491-2496, 1992.

D.I. Gittins et al., Diode-like electron transfer across nanostructured films containing a redox ligand, J. Mater. Chem., vol. 10, pp. 79-83, 2000.

E.V. Dehmlow & A. Sleegers, Synthesesn vol hyroxilierten Bipuridinen, III: Synthese vol unsymmetrischen und symmeterischen Dihydroxybipuridinen, Liebigs Ann. Chem. 9, pp. 953-959, 1992.

H. Fischer & A.L. Summers, Synthesis, polarography and hervicidal activity of quaternary salts of 2-(4-pyridyl)-1,3,5,5-triazines, 5-(4-pyridyl) pyrimidine, 2-(4-pyridyl) pyrimidine and related compounds, J. Heterocycl. Chem. 17(2), pp. 333-336, 1980.

E.W. Gill & A.W. Bracher, The synthesis and characterization of some diazaphenanthrene derivatives, J. Heterocyclic Chem. 20, pp. 1107-1109, 1983.

D.W. Turner et al., Molecular Photoelectron Spectroscopy, Wiley, Loneon 1970.

A. Ulman, Formation and Structure of Self-Assembled Monolayers, Chem. Rev., vol. 96(4). 1533-1554 (1996).

* cited by examiner (201)

2,7-Diazapheneanthrene (205)

2,7-Diazapyrene (206)

Tetrahydrodiazapyrene (207)

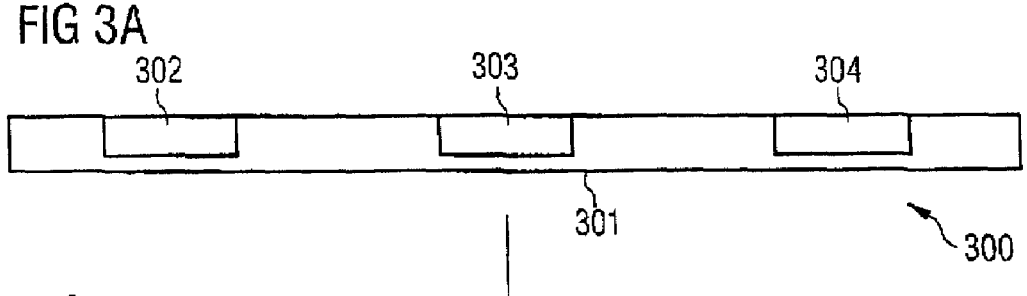
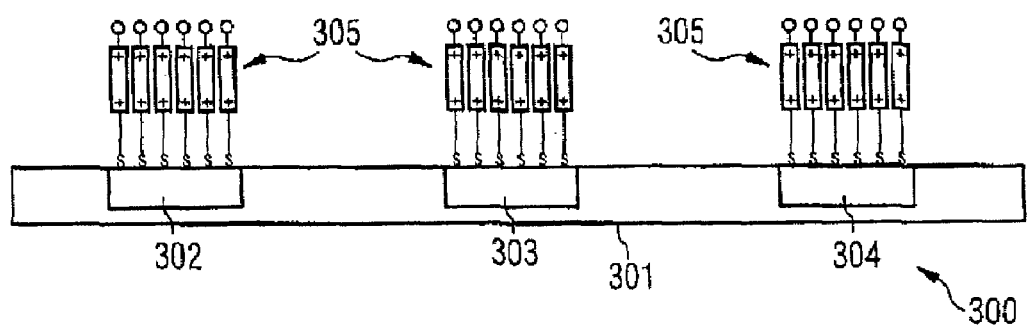
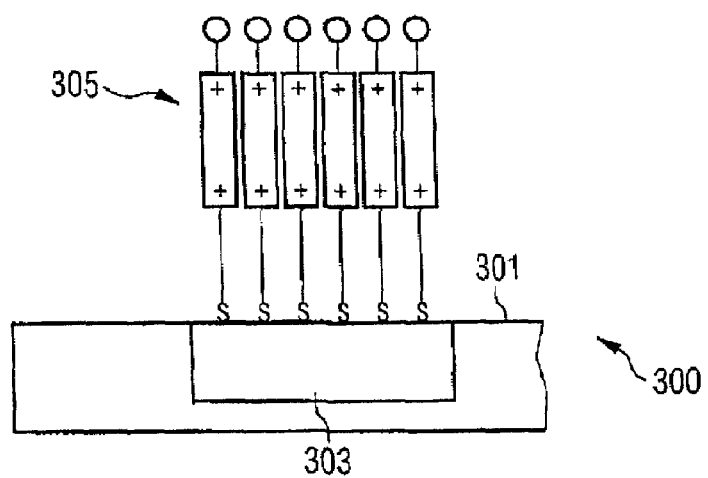

US 6,998,637 B2

CIRCUIT ELEMENT HAVING A FIRST LAYER COMPOSED OF AN ELECTRICALLY INSULATING SUBSTRATE MATERIAL, A METHOD FOR PRODUCING A CIRCUIT ELEMENT, BISPYRIDINIUM COMPOUNDS AND THEIR USE IN CIRCUIT ELEMENTS

BACKGROUND OF THE INVENTION

The invention relates to a circuit element having a first layer composed of an electrically insulating substrate material, a method for a producing a circuit element, bispyridinium compounds and their use in circuit elements.

1. Field of the Invention

Conventional microelectronics, which are based on silicon components such as CMOS chips (CMOS: complementary metal-oxide-semiconductor), will also be reaching their limits as miniaturization progresses further. Molecular electronics are being discussed as one of the possible ways to reduce the size of components further.

In addition to the general problem of developing circuit elements with the aid of molecular electronics, a further aspect under consideration in this context is the development of alternatives to the previous semiconductor memory elements such as DRAMs (Dynamic Random Access Memories), SRAMs (Static Random Access Memories) or Flash memories.

2. Description of the Related Prior Art

It is known from [1] that monomolecular layers based on rotaxanes can be used to produce configurable circuit elements which can be used to form logic gates. This is based on the fact that the monomolecular layers of the rotaxanes can be changed, that is to say "switched", from a conductive state to a less conductive state by application of a voltage. However, this switching process as is known from [1] is irreversible and is thus suitable for a write once/multiple read application.

It is known from [2] that a reversible switching process can be achieved with the aid of a further specific molecule class, which are referred to as catenanes. However, very low signals are observed during this switching process. Furthermore, [22] describes the use of specific catenanes in circuit elements which have a monomolecular layer composed of these catenanes.

However, the two circuit elements which are known from [1] and [2] also have further disadvantages for widescale practical use. On the one hand, rotaxanes and catenanes are available only by complex synthesis processes. On the other hand, Langmuir-Blodgett methods are used to produce the monomolecular layers for both circuit elements. Furthermore, the suitability of these Langmuir-Blodgett methods for the coating of surfaces of components such as silicon wafers, which are normally used for producing electrical components, is still uncertain.

In addition to the approaches just discussed for development of circuit elements based on organic molecular layers, it is known from [3] for an electrical switch to be produced by the specific combination of a molecule with a bispyridinium unit and a nanoparticle (metal cluster) composed of gold. Since nanotechnology is still in its infancy, it is questionable whether this system can be used for a practical application in the foreseeable future.

Furthermore, [23] describes a molecular electronic arrangement in which, although redox-active bispyridinium molecules can be used, the arrangement has a spacer between two conductor tracks, however.

A memory cell is also known from [24] which comprises at least four electrically conductive layers arranged one above the other.

Furthermore, the Laid-Open Specification [25] discloses electrochrome compounds and electrochrome apparatuses based on these compounds. In a similar way to [25], [26] discloses soluble polymers and their use in electrochrome apparatuses. Finally, [27] discloses photosensitizers based on ruthenium (II) complexes.

BRIEF SUMMARY OF THE INVENTION

The invention is based on the problem of providing alternative electrical circuit elements, as well as methods for their production.

The problem is solved by the circuit element and the method having the features as claimed in the independent patent claims.

A circuit element such as this is a circuit element having a first layer composed of an electrically insulating substrate material and having a first electrically conductive material. This first electrically conductive material is in the form of at least one discrete area such that it is embedded in the substrate material and/or is applied to the substrate material.

The circuit element also has a second layer having a second electrically conductive material, and a monomolecular layer composed of redox-active bispyridinium molecules, which is arranged between the first layer composed of the electrically insulating substrate material and the second layer with the second electrically conductive material. In this case, the bispyridinium molecules in the monomolecular layer are immobilized on the electrically conductive material which is in the form of at least one discrete area. In this case, the bispyridinium molecules in the monomolecular layer furthermore make electrical contact with the second electrical material of the second layer.

Furthermore, electrically inert molecules in the circuit element are immobilized on the first layer which is composed of these electrically insulating substrate material, which inert molecules form a matrix which surrounds the at least one discrete area with the monomolecular layer composed of bispyridinium molecules.

Here, the expressions redox-active bispyridinium molecule and redox-active bispyridinium compound in mean a chemical compound which can gain and lose electrons reversibly, that is to say in chemical terms its oxidation state can be changed by reduction and oxidation, and wherein a bispyridinium unit (see FIGS. 1, 2) can be used as the electron acceptor and/or electron donator. During this redox process of the bispyridinium unit or group, which is also referred to by the abbreviation "bipy", this is present either in the form of a double-positively charged cation or, after electron uptake, as a single-positively charged radical cation. This redox process can be described by the reaction equation $bipy^{2+} + e^- \rightleftharpoons bipy^+$.

In general, any compound with one or more bispyridinium units which can reversibly pass through the two oxidation states described above can be used as a functional unit in a circuit element as described here.

In one preferred embodiment, these bispyridinium molecules are compounds with the general formula (I)

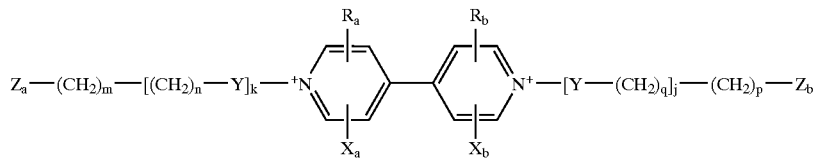

wherein in the formula (I), one or more of the carbon atoms of the two aromatic ring systems of the bispyridinium unit can be replaced independently of one another by (at least) one grouping $X_a$ or $X_b$ which in each case represents a heteroatom which is chosen from S, N and O, or which represents a blank (i.e. results in the production of a 5-ring)

one or more of the carbon atoms of the two ring systems may, in each case independently of one another, may have a substituent $R_a$ or $R_b$ which in each case independently represents alkyl, aryl, alkylaryl, alkenyl, alkynyl, halogen, CN, OCN, NCO, COOH, COOR', CONHR', $NO_2$, OH, OR', $NH_2$, NHR', NR'R", SH and SR', where R' and R" may independently of one another be alkyl, aryl, alkylaryl, alkenyl or alkynyl, or wherein $R_a$ and $R_b$ may together form a bridge between the two aromatic ring systems, which bridge comprises 1 to 3 atoms, wherein the atoms are chosen independently of one another from C, S, N and O, and may be linked linked to one another by a single, double or triple bond and, furthermore, may have a substituent $R_c$, with the substituent $R_c$ having the meaning indicated above for $R_a$ and $R_b$, Y represents a group which can be chosen independently of one another from $CH_2$, O, S, NH, NR', COO, CONH, CH=CH, C≡C or aryl, $Z_a$ and $Z_b$ may in each case independently of one another be $CH_3$, —CH=$CH_2$, SH, —S—S—, —S(CO)—$CH_3$, $SiCl_3$, $Si(OR)_3$, $SiR(OR')(OR")$, $SiR(OR')_2$, $Si(R'R")NH_2$, COOH, $SO_3$, $PO_3H$ or $NH_2$, wherein R' and R" may each independently of one another be alkyl, aryl, arylalkyl, alkenyl or alkynyl, wherein n, q may in each case independently of one another assume a value between 0 and 12, j and k may in each case independently of one another assume a value between 0 and 6, and p and m may in each case independently of one another assume a value between 0 and 12.

Compounds are preferred in which the chain which is bonded to the nitrogen atom of the respective ring in each case has no more than a total of 20 atoms. In this case, once again, compounds are preferred in which, overall, both chains together have a total length of no more than 30 atoms. Expressed with the aid of the indices, this means that (j·q+p) and (k·n+m) will preferably each assume a value (integer) of not greater than 20, independently of one another. The sum of (j·q+p)+(k·n+m) is in this case preferably not greater than 30. For the sake of clarity, it should be stressed here that the group Z is ignored in this consideration of the chain length of the two substituents which are bonded to the N atoms (see the detailed definition of Z which follows further below).

Since the bispyridinium compounds used here are generally present in cationic form, the bispyridinium compounds are used in the form of their suitable salts. Suitable counter-ions are, for example, the hydroxide anion ($OH^-$), the anions of the halogenides, in particular $Br^-$ and $Cl^-$, anions of organic acids such as acetate or complex anions such as the $PF_6^-$ anion, or other complex anions such as the anions of strong acids such as $NO_3^-$, $ClO_4^-$, or $SO_4^{2-}$. Further examples of suitable anions are complex anions such as $BF_4^-$, $CF_3SO_3^-$ (triflate), $B(Ph)_4^-$ or complex metal anions such as $[PtCl_4]^{2-}$.

Alkyl groups in the compounds of formula (I) or (II) as described here may be in the form of straight chains or branched chains, substituted or unsubstituted. This is also true when they occur in other groups, for example in alkoxy, alkylmercapto, alkoxycarbonyl groups. Alkyl groups with 1 to 12 carbon atoms are preferred, and alkyl groups with 1 to 8 carbon atoms are particularly preferred, especially in the compounds according to formula (I). The expression alkyl also comprises cycloalkyl groups with 3 to 8 ring carbon atoms, which may likewise be substituted or unsubstituted.

Alkenyl and alkynyl groups in the compounds in formula (I) or (II) can likewise be in the form of straight chains or branched chains, substituted or unsubstituted. This is still true when they occur in other groups, for example in alkoxy, alkylmercapto, alkoxycarbonyl groups. Alkenyl or alkynyl groups with 2 to 12 carbon atoms are preferred, and alkenyl or alkynyl groups with 2 to 8 carbon atoms are particularly preferred, especially in the compounds according to formula (I). The expression alkenyl also comprises cycloalkenyl groups with 3 to 8 ring carbon atoms, which may likewise be substituted or unsubstituted.

One substituent that is preferred here of the alkyl, alkenyl or alkynyl groups is halogen, i.e fluorine, chlorine, bromium or iodine, with fluorine being particularly preferred.

When $R_a$ and $R_b$ together form a bridge between the two ring systems of the compounds according to formula (I), it should be stressed at this point that, in this case, an HC=CH group represents a preferred alkenyl group, which preferably forms a bridge between the ring atoms 2 and 9 and/or 4 and 5. Accordingly, condensed aromatic systems such as 2,7-diazapheneanthrene (in the case of only one bridge) or 2,7-diazapyrenium (in the case of two bridges) are included in the basic bispyridinium skeletons that are preferably used here (see FIG. 2). Likewise (condensed) heterocyclic compounds derived therefrom can be used in the present invention (see definition of $R_a$ and $R_b$). A further exemplary basic bispyridinium skeleton in which the substituents Ra and Rb form a bridge is the tetrahydrodiazapyrene known from [4] (see FIG. 2). For the sake of clarity, it shall be stated such systems may of course also have a substituent $R_c$, as can be seen from the definition of formula 1. In one embodiment $R_c$ is preferably halogen, with fluorine once again being preferred.

The meaning of aryl in the compounds in formula (I) comprises substituted and unsubstituted carbocyclic aromatic groups such as phenyl, naphthyl, anthracyl as well as heterocyclic aromatic groups such as N-imidazolyl, 2-imi dazolyl, 2-thienyl, 3-thienyl, 2-furanyl, 3-furanyl, 2-pyridyl, 3-pyridyl, 4-pyridyl, 2-pyrimidyl, 4-pyrimidyl, 2-pyranyl, 3-pyranyl, 4-pyranyl, 3-pyrazolyl, 4-pyrazolyl, 5-pyrazolyl, 2-pyrazinyl, 2-thiazolyl, 4-thiazolyl, 5-thiazolyl, 2-oxazolyl, 4-oxazolyl and 5-oxazolyl. Ar likewise comprises condensed polycyclic aromatic ring systems such as quinoline or 9H-thioxanthene-10,10-dioxide, in which a carbocyclic aromatic ring is condensed with one or more heterocyclic rings.

The present invention also relates to novel bispyridinium compounds with the general formula (Ib)

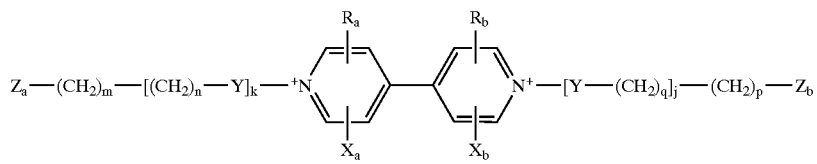

wherein in formula (Ib)

(at least) one grouping $X_a$ and/or $X_b$ can be replaced, which grouping in each case represents one heteroatom which is chosen from S, N and O, or represents a blank (that is to say which results in the generation of a 5-ring)

one or more of the carbon atoms of the two ring systems, in each case independently of one another, has a substituent $R_a$ or $R_b$ which in each case independently represents alkyl, aryl, alkylaryl, alkenyl, alkynyl, halogen, CN, OCN, NCO, COOH, COOR', CONHR', $NO_2$, OH, OR', $NH_2$, NHR', NR'R", SH and SR', where R' and R" may independently of one another be alkyl, aryl, alkylaryl, alkenyl or alkynyl, or wherein $R_a$ and $R_b$ together form a bridge between the two aromatic ring systems, which bridge comprises 1 to 3 atoms, wherein the atoms are chosen independently of one another from C, S, N and O, and may be linked to one another by a single, double or triple bond and, furthermore, may have a substituent $R_c$, with the substituent $R_c$ having the meaning indicated above for $R_a$ and $R_b$, Y represents a group which can be chosen independently of one another from $CH_2$, O, S, NH, NR', COO, CONH, CH=CH, C≡C or aryl, $Z_a$ and $Z_b$ may in each case independently of one another be $CH_3$, —CH=$CH_2$, SH, —S—S—, —S(CO)—$CH_3$, $SiCl_3$, $Si(OR)_3$, $SiR(OR')(OR")$, $SiR(OR')_2$, $Si(R'R")NH_2$, COOH, $SO_3$, $PO_3H$ or $NH_2$, wherein R' and R" may each independently of one another be alkyl, aryl, arylalkyl, alkenyl or alkynyl, wherein n, q may in each case independently of one another assume a value between 0 and 12, j and k may in each case independently of one another assume a value between 0 and 6, and p and m may in each case independently of one another assume a value between 0 and 12, wherein the following compounds are excluded:
N,N'-dimethyl-4,5,9,10-tetrahydro-2,7-diazapyreniumdiiodide (described in [4]);
1,1',2,2'-tetramethyl-4,4'-bispyridinium; 1,1',2-trimethyl-4,4'-bispyridinium (described in [5] and [6]);
N,N'-dimethyl-2,7-diazapyrenium (described in [7]);
N-methyl-N'-(p-toloyl)-2,7-diazapyrenium (described in [7]);
1,1'-dimethyl-2-phenyl-6-(p-toloyl)-4,4'-bispyridiumdiperchlorate (described in [8]);
1,1'-dimethyl-2-phenyl-4,4'-bispyridiumdiperchlorate (described in [8]);
6-(phenyl)-1,1',2-trimethyl-4,4'-bispyridiumdi-perchlorate (described in [8]);
1,1'-dimethyl-2-phenyl-6-(2,5-dichloro-3-thienyl)-4,4'-bispyridiumdiperchlorate (described in [8]).

Compounds are preferred in which the chain which is bonded to the nitrogen atom of the respective ring in each case has no more than a total of 20 atoms. In this case, once again, compounds are preferred in which both two chains together have a total length of no more than 30 atoms. Expressed with the aid of indices, this means that (j·q+p) and (k·n+m) can assume a value (integer) of not more than 20, preferably in each case independently of one another. The sum of (j·q+p) and (k·n+m) is thus in this case preferably not greater than 30.

The invention furthermore relates to the use of bispyridinium compounds with the general formula (I)/(Ib) as a functional component of (electrical) memory units, in particular as a functional component of permanent memories.

The bispyridinium compounds according to the formula (I) or (Ib) are preferably prepared in steps in that the bispyridinium unit is first synthesized and the quaternization on the nitrogen atom then takes place. In this case, unsubstituted bispyridine can be prepared by analogy to the biphenyls, for example by means of Ullmann coupling (C—C linking of aryl halogenides with copper) or Wurtz synthesis (step by step conversion with copper, which allows the formation of asymmetric compounds), in this context see, for example, [9] and the references cited therein. Unsubstituted bispyridine is commercially available.

The N-substituents are bonded to the bispyridium unit by a simple quaternization with R—X. For the simplest case, for example by conversion of bipyridyl with reactants such as methyliodide in benzole (see, for example, [10] or [11]). This then directly results in the symmetrically N-substituted bispyridinium compounds or, if a suitable residue X is used, also step by step in asymmetric compounds (the choice of X in this case controls the solubility in suitable solvents) and is followed by replacement of the counter-ion and substitution at the second N atom. In general, this can be formulated as follows:

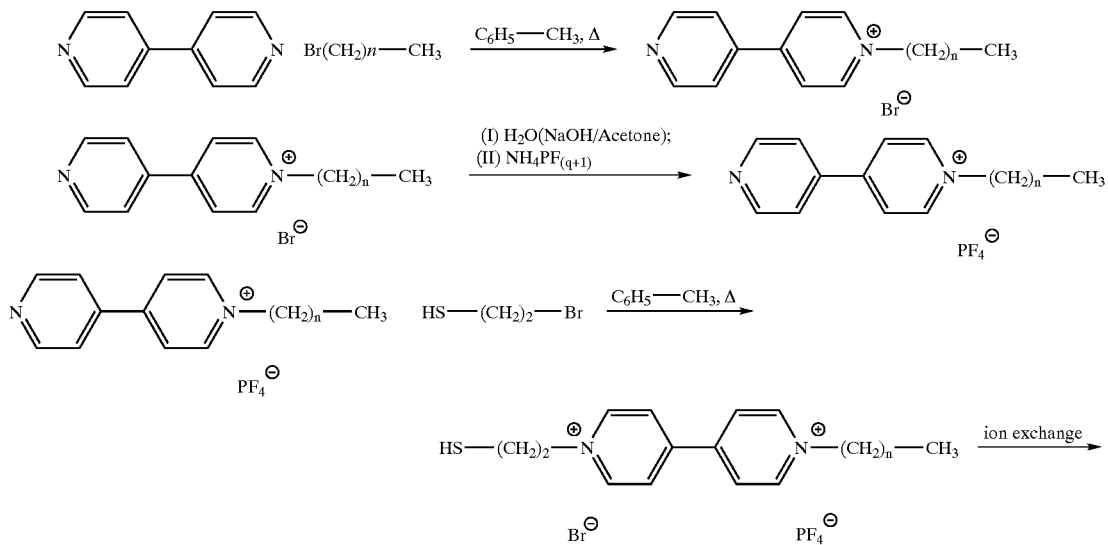

The substitution at the nitrogen atoms, which leads to asymmetric compounds, may, for example, be carried out in a two-step reaction process, such as that described in [12] on the basis of the synthesis of N-(n-decyl)-N'-(10-mercaptododecyl)-4,4'-bispyridinium (in this context, see also [13] or [14] as well as [15]).

The substitution of the bispyridinium unit by $R_a$ and $R_b$, in which case these may be both substituents with electron-donating characteristics and electron-withdrawing characteristics, can be carried out as a preceding reaction as described, for example, in [16], [17] or [18] (see in particular [16], schemes 1 and 2; [17] compounds 6). Starting from a bispyridinium compound which has a hydroxyl group in the 2-position (see R2 in [17]), it is also possible, for example, to achieve an —S—S— or —S— bridged system (see the definition of $R_a$ and $R_b$) by reaction with $P_2S_5$ and under ring formation. Furthermore, and in particular when using 2,7-diazapheneanthrene as the bispyridinium unit, the introduction of the substituents $R_a$ and $R_b$ can be carried out analogously to the method described in [19] (see in particular the compounds 6 and 7 there).

Compounds with (additional) heteroatoms, i.e. one or more groups X, may, for example, be obtained by means of the synthesis process described in [18] (see blocks 4 and 5 there).

In the compounds according to formula (I)/(Ib), the group X and the substituents R can be used to influence and to deliberately control the electrochemical characteristics, i.e. in particular the redox potentials of the bispyridinium unit. Substitutions such as these can assist the charge equalization during a switching process in the circuit element.

It is thus possible to simplify the electron release by the bispyridinium unit, for example by substituents R which are rich in electrons, such as alkyl or alkyl residues, which exert an inductive, electron-donating effect (referred to as the +I effect), and in this way decrease the reduction potential. The same is true for substituents which place free electron pairs at disposal and allow the formation of resonance structures, i.e. which show an +M effect. Examples of such substituents are —OH, —OR, —NH$_2$, —NHR, —SR or fluorine.

Effects in the opposite sense, i.e. increasing the oxidation potential, can be achieved by substituents with electron-withdrawing −I and −M effects (for example —CN, —NO$_2$, —COOH, —SO$_3$H) or substituents such as chlorine, in which an electron-withdrawing effect prevails over an electron-donating effect.

These effects should be derivable and be in good agreement, for example, with trends and knowledge from photo-electron spectroscopy (see, for example, [20]). For example, the ionization potential for substituted benzenes is known from this, and is correlated with the energy of the highest occupied molecule orbital (HOMO). +I and +M substituents have higher-energy HOMOs than benzene, i.e. lower ionization potentials (corresponding to them being easier to oxidize), with the effect being reversed in the case of −M and −I substituents. This influence on the ionization potentials is admittedly not quite as strong, but is still significantly present. This relationship should be true in particular because the electrophilic aromatic substitution with the reaction-accelerating influence of +M/+I substituents takes place via a primary reaction of the aromatic electron system with $E^+$, i.e. it corresponds to an oxidation of the aromatic.

The substituent Y can likewise be used to influence the electrochemical characteristics of the bispyridinium compounds used here, in the manner as described above for the substituents R and X.

One preferred class of bispyridinium compounds is molecules with long-chain alkyl residues. These compounds have the advantage that they allow the formation of self-organizing layers of the redox-active molecules on the surface of the electrically conductive material. With compounds such as these, j and k in the formula (I) assume the values 0.

In one embodiment, molecules are preferred in the present inventions in which the (alkyl) chains which are located on the pyridine nitrogen atom have a length of 6 to 12 atoms. However, it is also possible to use shorter or longer chains, provided that the redox characteristics of the bispyridinium molecules and the functionality of the circuit element are not adversely affected by this.

The letter Z in the formula (I) represent a head group or anchor group, by means of which the bispyridinium compounds are applied to the electrically conductive materials. This immobilization can be carried out by physical or chemical interactions.

These interactions include hydrophobic or ionic (electrostatic) interactions and covalent bonds. For example, when using thiol groups as substituent and gold as the conductive material which is applied to the substrate material, the immobilization is carried out by means of what is referred to as gold-sulfur coupling.

When using groups such as SH, $SiCl_3$ or $NH_2$, COOH, a direct covalent bond can be produced between the bispyridinium compound and the electrically conductive material. In this case, it is also possible to use disulfide compounds (RSSR', where R=R'=a molecule containing bipyridyl, and R=a molecule containing bipyridyl, and R' is simply methyl or short alkyl), which likewise form monolayers on gold, but carry this out by means of interactions that are not covalent. It is also possible, for example when free hydroxyl groups can be formed on the surface of the electroconductive material (for example when using doped silicon), to use alkoxy silanes for the linkage, for example $—SiR_n(OR')_{3-n}$ with R and R' alkyl, R' typically methyl or ethyl, n=0–2.

The covalent bonding may in this case be carried out using any suitable bonding chemistry. However, it is also possible to use a short separate linker for immobilization of the redox-active compounds.

The choice of the respective head group may also be influenced by the nature of the electrically conductive material. For example, in the case of gold as the conductive material, thiols are particularly suitable as anchor groups; when using palladium, cyanide and isocyanide may be used as preferred head groups and, for silicon surfaces, silylchloride, silylamine $Si(R'R'')NH_2$ and, as above, alkoxysilane, $—SiR'_n(OR'')_{3-n}$ with R' and R''=alkyl (typically methyl, ethyl, propyl, butyl, etc., n=preferably 0–5, and particularly preferably n=0–2) are particularly suitable anchor groups for immobilization.

Another head group which is generally highly suitable for immobilization and is thus likewise preferred is $—S(CO)—CH_3$.

In one embodiment of the circuit element, a covalent bond of the redox-active compounds to the first and/or to the second conductive material is preferred since this makes it possible to ensure the orientation of the molecules and the (electrical) contact to the conductive materials.

In this context, an electrically inert molecule is a chemical compound which is used as an electrical isolator and is preferably also chemically inert, in particular being resistant to oxidation or reduction, and which therefore does not interfere with the switching process which is generated by the redox-active bispyridinium molecules. Owing to their characteristic that they can be used as an electrical isolator, the layers composed of the inert molecules, which may in consequence also be referred to as isolator molecules, form an isolating matrix, in order to electrically isolate the individual active areas (positions) of the circuit element from one another.

In principle, it is possible to use any type of molecules in the circuit element according to the invention that satisfy the requirements that have just been mentioned. In this case, it is also possible to use different types of inert molecules in order to form an isolating matrix.

In one preferred embodiment of the circuit element, the electrically inert molecules are compounds with a long-chain (saturated) alkyl residue.

The electrical molecules preferably have a head group by means of which they can be bonded to the first layer which is composed of the electrically insulating substrate material. In this case, immobilization can be achieved by means of non-covalent bonds or covalent bonds. It is also possible to immobilize the inert molecules on the layer composed of the second electrically conductive material.

The inert matrix-forming molecules are preferably alkylsilyl compounds with the general formula $$CH_3—(CH_2)_p—SiR_1R_2R_3 \quad (II)$$

wherein in formula (II), p represents an integer between 1 and 30, and preferably 1 and 20, and wherein the inert molecules are immobilized on the first layer by means of at least one of the residues $R_1$, $R_2$ and $R_3$, which may independently of one another be hydrogen, halogen, OR', NHR', NR'R'', wherein R' and R'' is alkyl (typically methyl, ethyl, propyl, butyl, etc., n=preferably 0–5, particularly preferably n=0–2). Compounds such as these are commercially available, for example from ABCR/Gelest (with simpler compounds also being available from Fluka or Aldrich). These compounds are particularly preferred when a substrate based on silicon is used. In this case, a covalent bond is produced between the inert isolator molecules via free hydroxy groups on the surface of the substrate material.

At this point, it should be noted that the length of the alkyl chains of the electrically inert molecules depends on the respectively chosen bispyridinium compounds. It is advantageous for the length of the molecules to be approximately the same, in order in this way to achieve monomolecular layers with approximately the same thicknesses. The number of alkyl units in the isolating tail group of the inert isolator molecules can be estimated on the basis of the known bonding lengths. However, a purely empirical procedure can also be used to determine the most suitable molecule length.

In consequence, the use of electrically inert molecules with a long-chain alkyl residue, in particular of alkylsilyl compounds with the formula (II), in circuit elements is a further object of the invention.

In one embodiment, the circuit element disclosed here is an element in which a large number of discrete areas of the first electrically conductive material are embedded in the substrate material and/or are applied to the substrate material. This embodiment makes it possible, for example, to form the circuit element according to the invention as an electrical memory with a large number of memory cells.

In this context, it shall be mentioned that, of course, it is possible to apply not only different bispyridinium compounds to a single discrete area of the conductive first material. Furthermore, it is also possible to provide variations of these areas with different redox-active compounds, in order, in this way, to match the characteristics of the circuit element to a specific application.

In one preferred embodiment of the circuit element, the first electrically conductive material is gold, silver palladium, platinum or silicon. The discrete area which the first conductive material occupies may be in the form of an electrode in the substrate material.

In another embodiment of the circuit element disclosed here, the layer of the second electrically conductive material preferably comprises titanium and/or aluminum. The second layer may likewise be in the form of an electrode. Furthermore, the materials of the first electrode are suitable as further materials for forming the second electrode.

In one preferred embodiment, the circuit element described here is arranged between two electrodes. These electrodes may be the first and the second electrically conductive material. In this embodiment, i.e. when arranged between two electrodes, the circuit element in the present invention represents a variable resistor, and in consequence a memory element.

In a refinement in which a large number of redox-active bispyridinium layers are used, an arrangement of such memory elements forms a memory matrix, i.e. it can be used as an electrical memory. One advantage of this refinement is the use of a molecular two-pole as a memory element, whereby the wiring complexity is reduced and the packing density is increased in comparison with conventional memory elements such as RAMs. The memory element according to the invention thus offers access to a highly integrated electrical memory. The memory element is preferably a permanent memory element, and the electrical memory which is based on a large number of memory elements is preferably a permanent memory. A permanent memory such as this may, for example, be used as a memory for graphics information, for example as a memory for on-chip video films.

In the method according to the invention for producing a circuit element, a first layer of an insulating substrate material is provided, and a first electrically conductive material is embedded in the substrate material and/or is applied to the substrate material at at least one discrete position.

Redox-active bispyridinium molecules are then immobilized as the monomolecular layer on the at least one discrete area of the first electrically conductive material. Electrically inert molecules are then immobilized on the first layer of the electrically insulating substrate material. The electrically inert molecules thus form a matrix, which surrounds the at least one area with the monomolecular layer composed of bispyridinium molecules.

In the method, a second layer with a second electrically conductive material is then applied to the layer composed of the electrically inert molecules and the bispyridinium molecules. In consequence, the bispyridinium molecules in the monomolecular layer make contact with the second electrically conductive material of the second layer. The inert matrix-forming isolator molecules need not be immobilized on the second conductive material.

In one preferred embodiment, the bispyridinium compounds are, however, also immobilized on the second electrically conductive material, in order to ensure electrical contact with this material. This immobilization can be carried out on the basis of the identical head group Z in the same way as the immobilization on the first conductive material.

In the method, compounds with the general formula (I) are preferably used as bispyridinium molecules. Compounds with a long-chain alkyl residue, in particular compounds according to the formula (II), are preferably used as electrically inert molecules.

Gold is preferably used as the first conductive material. The first electrically conductive material is furthermore preferably embedded in and/or is applied to the substrate material in a regular arrangement.

The layer composed of the second electrical material is preferably applied in such a way that the second electrical material is vapor-deposited onto the layer composed of the electrically inert molecules and the bispyridinium molecules.

In a further embodiment of the method, titanium and/or aluminum are/is used as the second electrically conductive material.

Exemplary embodiments of the invention will be explained in more detail in the following text and are illustrated in the figures.

BRIEF DESCRIPTION OF THE DRAWINGS

FIGS. 3a to 3e show an exemplary embodiment of the method described here for producing a circuit element;

DETAILED DESCRIPTION OF THE INVENTION

Figure 1A:
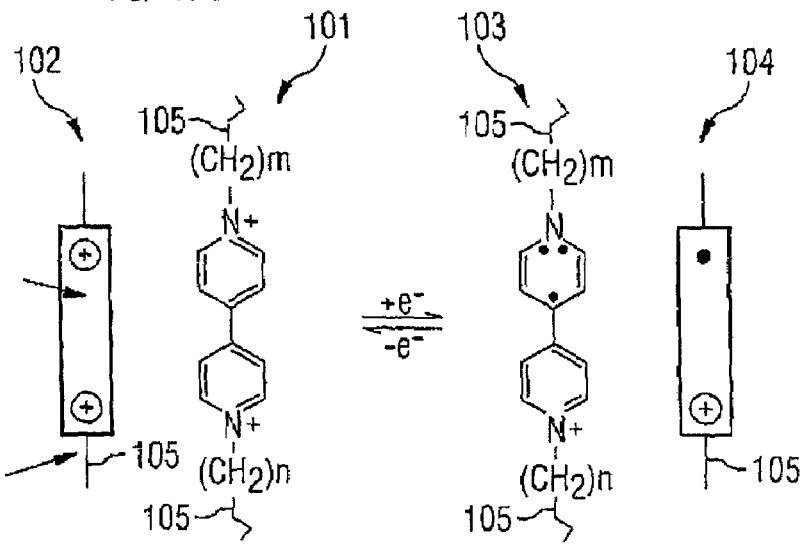
FIGS. 1a and 1b show the redox-active bispyridinium unit of the molecules used in the inventions, as well as a schematic illustration of the method of operation of a circuit element according to the invention.

FIG. 1a shows a representation of a formula as well as a schematic illustration of the bispyridinium unit, on the basis of which the redox process, which takes place at the molecular level, of the bispyridinium unit (of the bispyridinium basic skeleton) is illustrated.

The double-positively charged cation 101, which has the reference number 102 in the schematic illustration, is the species which is not conductive below a predetermined reduction potential.

Above this predetermined reduction potential, the cation 101 represents an electron acceptor. After accepting an electron, the doubly-positively charged cation changes to the singly-positively charged radical cation 103 (104 in the schematic illustration). The free electron makes the radical cation electrically conductive. This state is below the oxidation potential of the radical cation 103. Above the oxidation potential, the radical cation in consequence represents an electron donator. The alkyl chains which are identified by the reference symbol 105 and are bonded to the pyridine ring system via the nitrogen atom in the respective ring do not themselves take part in the redox process, but rather act as an isolator. However, substituents which are incorporated in the alkyl chains such as those described above may influence the position of the redox potential, for example by virtue of +M and/or +I effects.

Figure 1B:
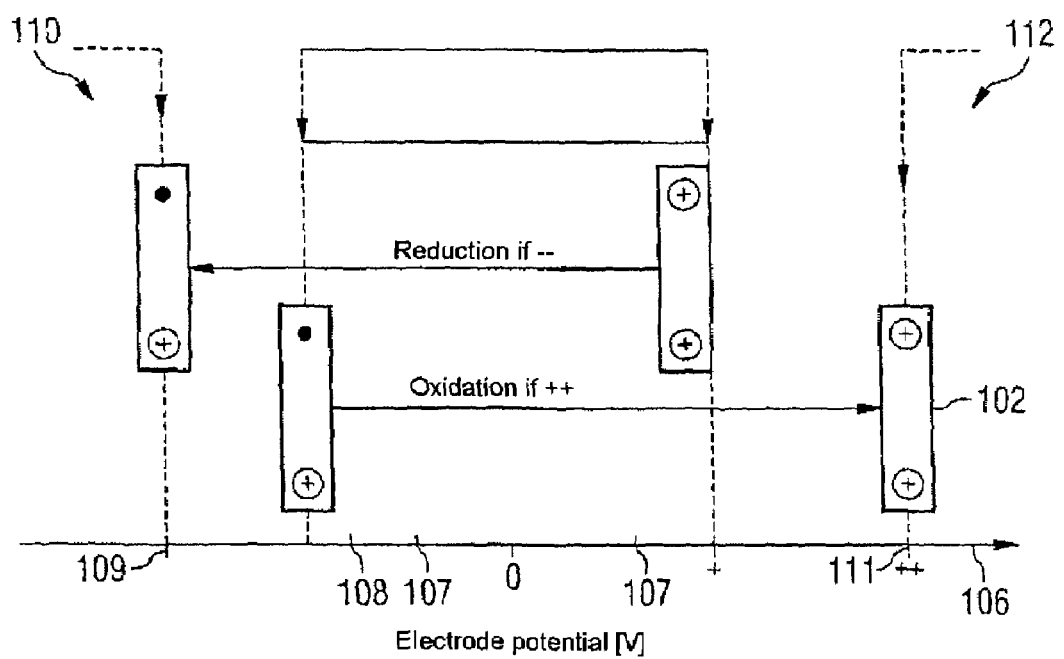

FIG. 1b shows, schematically, the potential conditions and the method of operation (the switching principle) of a circuit element according to the present invention, in the form of a memory element. This memory element may be a circuit element in which one area composed of the first electrically conductive material is used as an electrode, and the layer composed of the second electrically conductive material is used as an electrode.

When small positive or negative potentials 107 are applied (the potential is indicated in its relative position on the x axis 106), no changes to the redox state are initiated at this stage. This area 108 is used for reading the memory cell. The application of a higher negative potential 109 results in reduction of the molecule (transition to the radical cation 104). This area 110 is used for writing to the memory element. If a higher positive potential 111 is applied to the memory element, this results in oxidation of the molecule, that is to say conversion to the dication 102. This area 112, which starts with the potential 111, is used for erasing the memory element. Since this redox process is reversible, any desired number of write, read and erasure processes can be carried out.

Figure 2A:
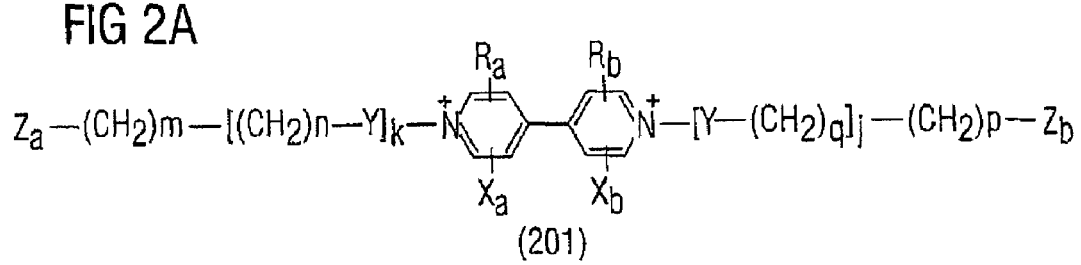
FIGS. 2a to 2e show representations of formulae for redox-active bispyridinium compounds which are used in a preferred manner in the invention, and of electrically inert molecules which are used in a preferred manner.
Figure 2B:
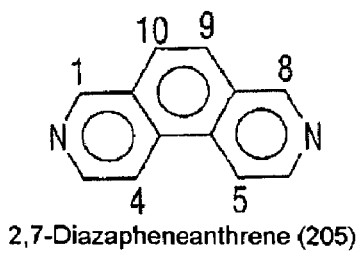
Figure 2C:
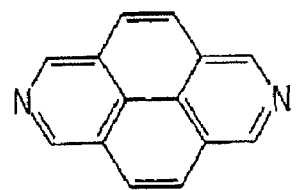
Figure 2D:
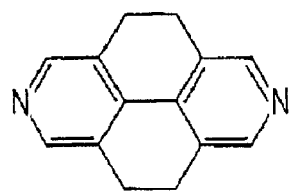
Figure 2E:
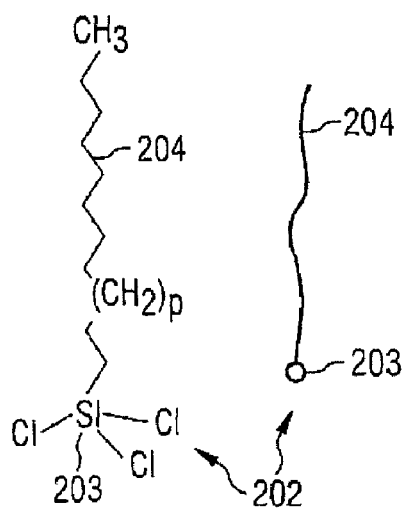

FIG. 2a shows bispyridinium compounds 201 according to formula (I), which are preferably used in the present invention. FIG. 2b to FIG. 2d show 2,7-diazapheneanthrene (205), 2,7-diazapyrenium (206) and tetrahydrodiazapyrene (207) as examples of a basic bispyridinium skeleton, in which the substituents $R_a$ and $R_b$ form a bridge. FIG. 2e shows the formula and, schematically, a trichloroalkylsilane compound 202, which represent a preferred embodiment of the electrically inert isolator molecules. The head group or anchor group for immobilization has the reference symbol 203, and the long-chain (isolating) alkyl chain has the reference symbol 204.

FIG. 3 shows an example of the method as described here for producing a circuit element 300.

FIG. 3a shows the substrate material 301 in which discrete areas 302, 303, 304 composed of the first electrically conductive material are arranged. The substrate material is an isolator material such as silicon oxide. The discrete areas 302, 303, 304 are composed of gold.

A redox-active bispyridinium compound 305 is then immobilized on the areas 302, 303, 304 (FIG. 3b, FIG. 3c), with a monomolecular layer composed of the molecules of the compound 305 being formed on each of these areas. The compound is in this case N,N-di-(10-mercaptodecyl)-4,4'-bispyridiniumdibromide, which can be synthesized as described in [15]. The immobilization on the gold surfaces of the areas 302, 304, 304 is in this case carried out via the gold-sulfur coupling (see the detailed view in FIG. 3c). The bispyridinium compound is normally for this purpose held in an organic solvent such as hexane or ethanol (depending on the solubility) in a concentration of 10 to 100 mM, and is brought into contact with the substrate surface. The adsorption then normally takes place in a time period of 30 minutes to about 12 hours (overnight) at room temperature. The surface is then carefully rinsed with solvent. The substrates which are provided with the monomolecular layers in this way can be stored well in air and in solvent (provided that the temperature is not too high). An overview of the immobilization methods which can be used here is offered [21].

Figure 3D:
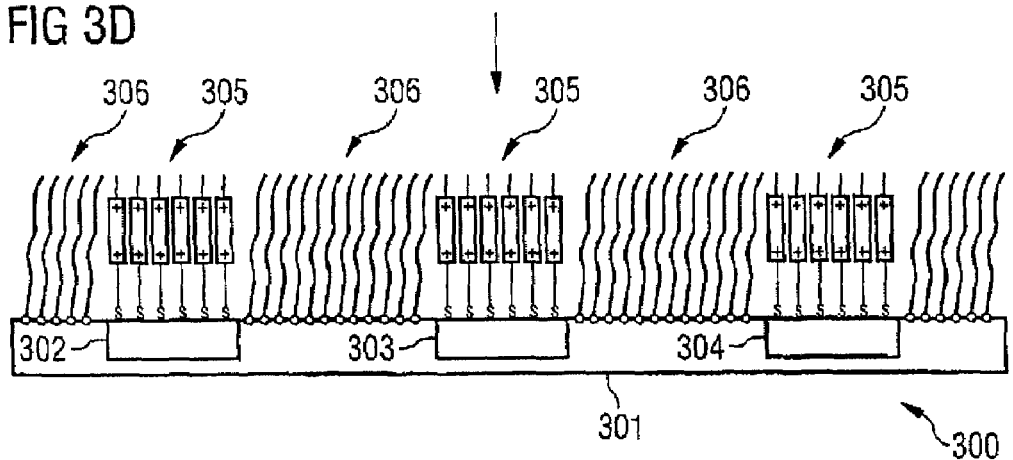

After this, electrically inert molecules 306 on the layer of the substrate material 301 are immobilized as monomolecular layer (FIG. 3d).

Trichloroalkylsilanes or alkoxysilanes with an alkyl chain length of about 10 to 30, preferably with up to about 20 carbon atoms, are in this case used as molecules 306. The immobilization is carried out by covalent bonds of the silicon atom with hydroxyl groups on the surface of the silicon dioxide which is used as the substrate material 301.

Figure 3E:
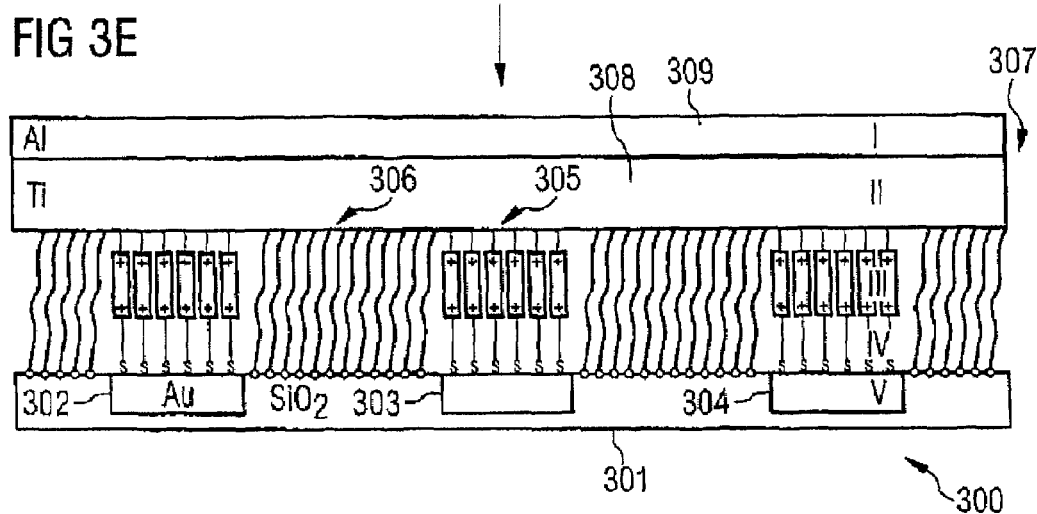

The second electrically conductive layer 307 of the circuit element is formed in the next step (FIG. 3e). For this purpose, a layer 308 composed of titanium is first of all vapor-deposited in a vacuum onto the monomolecular layers of the bispyridinium compounds 305 and of the isolator molecules 306. A further layer 309 composed of aluminum is then vapor-deposited in a vacuum. In principle, all methods which allow effective deposition of the metal layer can be used for applying the second electrical layer.

This results in the formation of a circuit element with a plurality of molecular resistors, and which can be used, for example, as a component of a memory cell.

Figure 4A:
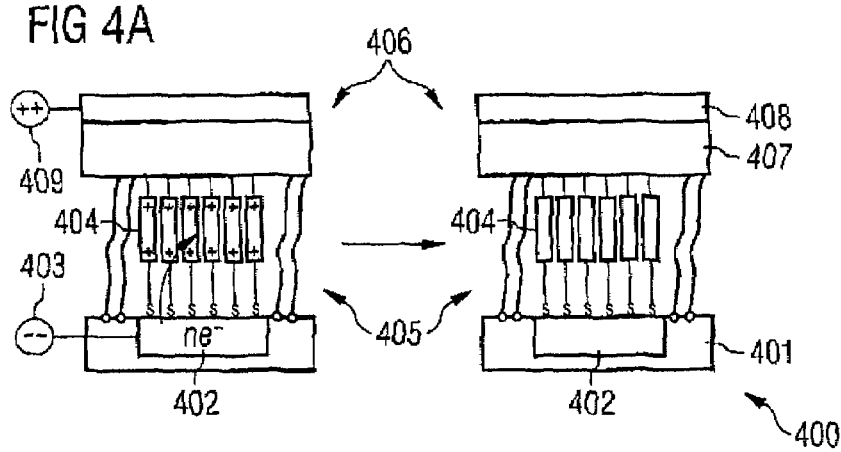
FIGS. 4a to 4c show an electrical memory, in which the circuit elements described here are used, as well as its method of operation.
Figure 4B:
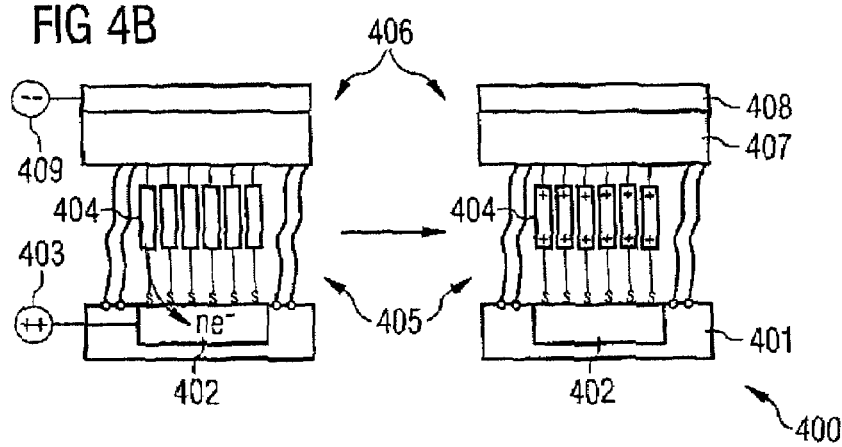
Figure 4C:
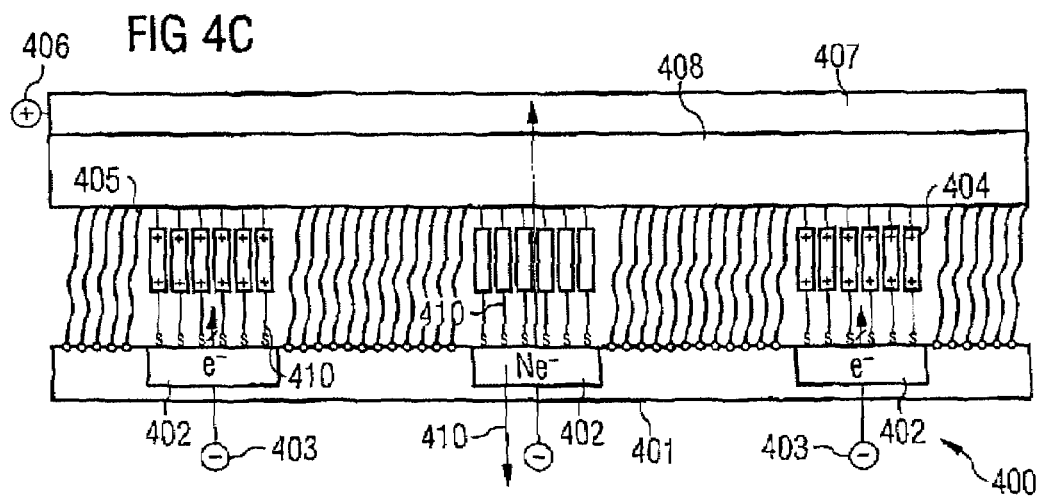

FIG. 4 shows a detail of an electrical nonvolatile memory 400 according to the present invention, which is based on a large number of the circuit elements as described here (see FIG. 4c).

The nonvolatile memory 400 has a substrate 401 composed of an isolator material, in which a large number of discrete areas 402 composed of a first conductive material are formed. The substrate/isolator material is silicon dioxide, and the first conductive material is gold. The discrete gold areas are provided with an electrical connection 403, i.e. is in the form of an electrode. A monomolecular layer composed of redox-active bispyridinium compounds 404 is immobilized on each of the gold areas 402. N-(n-decyl)-N'-(10-mercaptododecyl)-4,4'-bispyridinium is in this case used as the compound 404, and is obtained according to [12]. Alternatively, the compounds as described in [13] and [14] can also be used.

A layer composed of alkyltrichlorosilane compounds is immobilized on the substrate material 401, as electrically inert isolator molecules 405. In the present case, octadecyltrichlorosilane, $C_{18}H_{35}SiCl_3$, (commercially available, for example, from Aldrich) is used for this purpose.

The two molecule layers make contact with a second layer 406 composed of electrically conductive material, which has been applied to the molecule layers. The second layer 406 has a layer 407 composed of titanium and a layer 408 composed of aluminum. It is also provided with an electrical connection 409, and is thus in the form of an electrode.

FIG. 4a and FIG. 4b show the procedure for storing information by the memory 400. A negative potential which is greater than the reduction potential of the bispyridinium compounds is applied to a chosen layer of the redox-active bispyridinium compounds 404, for example via the electrical connection 403 (and the area 402 which forms an electrode). This leads to a voltage (write voltage) on the electrodes 403, 409 and to a write process, in which each bispyridinium unit absorbs one electron via the area 402 and changes to the form of the single-positively charged radical cation (cf., FIG. 1b).

The erasure process, which is likewise part of the process of storing information, takes place as follows.

A positive potential which is greater than the oxidation potential of the bispyridinium compounds is once again applied, for example, via the electrical connection 403 to a selected layer in the redox-active bispyridinium compounds 404. This is associated with a voltage (erasure voltage) on the electrodes 403, 409 and with an erasure process, in which each bispyridinium unit loses an electron by means of the area (the electrode) 402 and in the process changes to a double-positively charged dication.

In this context, it should be mentioned that the nonvolatile memory 400 and all other embodiments which make use of a large number of separate circuit elements according to the invention allow each circuit element and memory element to be driven/addressed individually.

The read process is shown in FIG. 4c. During this process, what is referred to as a read voltage is applied, which does not influence the redox state of the bispyridinium compounds 404 that are present at that time in the individual memory elements. This means that the applied potential difference produces neither oxidation nor reduction of the bispyridinium molecules in the individual separate memory elements. The read voltage leads to a current flowing through each memory element (symbolized by the arrows 410), whose magnitude is governed by the respective state of the charge in the memory elements, and which is used for further information processing.

In the case of molecule layers in which the bispyridinium molecules are in the form of dications, a smaller current, or no current at all, is measured in this case. In layers in which the bispyridinium units of the molecules are in the form of single-positively charged radical cations, a (greater) current flow is measured.

The nonvolatile memory 400 thus represents a small scaleable and addressable memory, whose physical construction is considerably simpler than that of conventional memories such as DRAMs or SRAMs, and which, for example, requires less wiring.

The invention claimed is:

1. A circuit element having a first layer composed of an electrically insulating substrate material, comprising:
   a first electrically conductive material, which is in the form of at least one discrete area such that it is embedded in the substrate material and is applied to the substrate material;
   a second layer having a second electrically conductive material; and
   a monomolecular layer composed of redox-active bispyridinium molecules, which is arranged between the first layer composed of the electrically insulating substrate material and the second layer with the second electrically conductive material, with the bispyridinium molecules in the monomolecular layer being immobilized on the electrically conductive material which is in the form of at least one discrete area, and with bispyridinium molecules in the monomolecular layer making electrical contact with the second electrical material of the second layer, wherein
   electrically inert molecules are immobilized on the first layer which is composed of the electrically insulating substrate material, and which molecules form a matrix which surrounds the at least one discrete area with the monomolecular layer composed of bispyridinium molecules.

2. The circuit element as claimed in claim 1, further comprising the bispyridinium molecules being two-aromatic-ring compounds with the general formula (I),

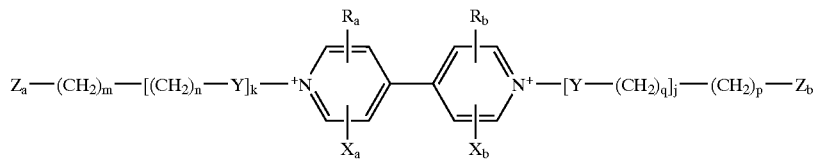

wherein in formula (I),
   at least one of the carbon atoms of the two aromatic ring systems of the bispyridinium unit can be replaced independently of one another by at least one grouping $X_a$ and $X_b$ which in each case represents a heteroatom which is selecting from the group consisting of S, N, O and a blank;
   at least one of the carbon atoms of the two ring systems may, in each case independently of one another, have a substituent $R_a$ and $R_b$ selected from the group consisting of alkyl, aryl, alkylaryl, alkenyl, alkynyl, halogen, CN, OCN, NCO, COOH, COOR', CONHR', NO$_2$, OH, OR', NH$_2$, NHR', NR'R'', SH and SR', wherein R' and R'' is selected from the group consisting of alkyl, aryl, alkylaryl, alkenyl and alkynyl;

Y is selected from the group consisting of CH$_2$, O, S, NH, NR', COO, CONH, CH=CH, C≡C and aryl;

$Z_a$ and $Z_b$ are selected from the group consisting of CH$_3$, —CH=CH$_2$, SH, —S—S—, —C(CO)CH$_3$, SiCl$_3$, Si(OR)$_3$, SiR(OR')(OR''), SiR(OR')$_2$, Si(R'R'')NH$_2$, COOH, SO$_3$, PO$_3$H and NH$_2$, wherein R' and R'' are selected from the group consisting of alkyl, aryl, arylalkyl, alkenyl and alkynyl; and wherein n and q may in each case independently of one another assume a value between 0 and 12,
j and k may in each case independently of one another assume a value between 0 and 6, and
p and m may in each case independently of one another assume a value between 0 and 12.

3. The circuit element as claimed in claim 1 or 2, in which the electrically inert molecules are compounds with a long-chain alkyl residue.

4. The circuit element as claimed in claim 3, in which the inert molecules have a head group by means of which they are covalently bonded to the first layer which is composed of the electrically insulating substrate material.

5. The circuit element as claimed in claim 4, in which the inert molecules are alkylsilyl compounds with the general formula $$CH_3—(CH_2)_p—SiR_1R_2R_3 \qquad (II),$$

wherein in formula (II) p represents an integer between 1 and 30, and wherein $R_1$, $R_2$ and $R_3$ are selected from the group consisting of hydrogen, halogen, OR', NHR', and NR'R'', and wherein R' and R'' is equally alkyl.

6. The circuit element as claimed in claim 1, further comprising a plurality of discrete areas which are composed of the first electrically conductive material are embedded in the substrate material and are applied to the substrate material.

7. The circuit element as claimed in claim 1, in which the first electrically conductive material is selected from the group consisting of gold, silver palladium, platinum and silicon.

8. The circuit element as claimed in claim 1, in which the layer which is composed of the second electrically conductive material comprises titanium and aluminum.

9. The circuit element as claimed in claim 1, further comprising the first electrically conductive material and the second electrically conductive material being in the form of electrodes.

10. The circuit element as claimed in claim 9, further comprising the circuit element being a memory element.

11. The circuit element as claimed in claim 10, further comprising the circuit element being a nonvolatile memory.

12. A method for producing a circuit element, comprising:
   providing a layer composed of an insulating substrate material;

embedding a first electrically conductive material in the substrate material and is applied to the substrate material at at least one discrete position;

immobilizing redox-active bispyridinium molecules as monomolecular layer on the at least one discrete area which is composed of the first electrically conductive material;

immobilizing electrically inert molecules on the first layer which is composed of the electrically insulating substrate material, whereby the electrically inert molecules form a matrix which surrounds the at least one area with the monomolecular layer composed of bispyridinium molecules; and applying a second layer with a second electrically conductive material to the layer composed of the electrically inert molecules and the bispyridinium molecules, whereby the bispyridinium molecules in the monomolecular layer make contact with the second electrical material of the second layer.

13. The method as claimed in claim 12, in which compounds with the general formula (I)

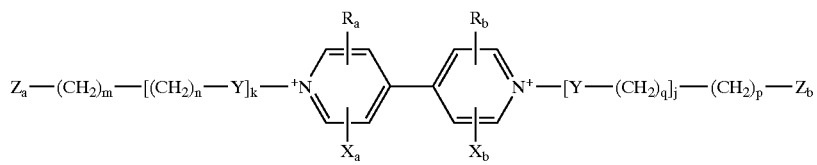

are used as bispyridinium molecules, wherein in the formula (I), at least one of the carbon atoms of the two aromatic ring systems of the bispyridinium unit can be replaced independently of one another by at least one grouping $X_a$ and $X_b$ which in each case represents a heteroatom which is selected from the group S, N, O and a blank, consisting of at least one of the carbon atoms of the two ring systems may, in each case independently of one another, have a substituent $R_a$ and $R_b$ selected from the group consisting of alkyl, aryl, alkylaryl, alkenyl, alkynyl, halogen, CN, OCN, NCO, COOH, COOR', CONHR', $NO_2$, OH, OR', $NH_2$, NHR', NR'R", SH and SR', wherein R' and R" are selected from the group consisting of alkyl, aryl, alkylaryl, alkenyl and alkynyl;

Y is selected from the group consisting of $CH_2$, O, S, NH, NR', COO, CONH, CH=CH, C≡C and aryl;

$Z_a$ and $Z_b$ are selected from the group consisting of $CH_3$, —CH=$CH_2$, SH, —S—S—, —C(CO)$CH_3$, $SiCl_3$, Si(OR)$_3$, SiR(OR')(OR"), SiR(OR')$_2$, Si(R'R")$NH_2$, COOH, $SO_3$, $PO_3$H and $NH_2$, where R' and R" are selected from the group consisting of alkyl, aryl, arylalkyl, alkenyl and alkynyl; and wherein n, q may in each case independently of one another assume a value between 0 and 12, j and k may in each case independently of one another assume a value between 0 and 6, and p and m may in each case independently of one another assume a value between 0 and 12.

14. The method as claimed in claim 12 or 13, in which compounds with a long-chain alkyl residue are used as electrically inert molecules.

15. The method as claimed in claim 12, in which gold is used as the first conductive material.

16. The method as claimed in claim 12, in which the first electrically conductive material is embedded in and is applied to the substrate material in a regular pattern.

17. The method as claimed in claim 12, in which the second electrical material is vapor-deposited onto the layer composed of the electrically inert molecules and the bispyridinium molecules.

18. The method as claimed in claim 17, in which the second electrically conductive material is selected from the group consisting of titanium and aluminum.

19. A bispyridinium compound having the general formula (Ib)

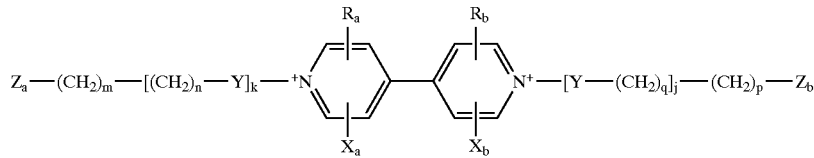

wherein in formula (Ib)

at least one of the carbon atoms of the two aromatic ring systems of the bispyridinium unit can be replaced independently of one another by at least one grouping $X_a$ and $X_b$, which in each case represents a heteroatom which is chosen from S, N and O, or which represents a blank, at least one of the carbon atoms of the two ring systems, in each case independently of one another, has a substituent $R_a$ and $R_b$ are selected from the group consisting of alkyl, aryl, alkylaryl, alkenyl, alkynyl, halogen, CN, OCN, NCO, COOH, COOR', CONHR', $NO_2$, OH, OR', $NH_2$, NHR', NR'R", SH and SR', wherein R' and R" are selected from the group consisting of alkyl, aryl, alkylaryl, alkenyl and alkynyl;

Y represents a group selected from the group consisting of CH$_2$, O, S, NH, NR', COO, CONH, CH=CH, C≡C and aryl;

Z$_a$ and Z$_b$ are selected from the group consisting of CH$_3$, —CH=CH$_2$, SH, —S—S—, SiCl$_3$, Si(OR)$_3$, SiR(OR') (OR"), SiR(OR')$_2$, Si(R'R")NH$_2$, Si(R$_2$')NH$_2$, COOH, SO$_3$, PO$_3$H and NH$_2$, wherein R' and R" are selected from the group consisting of alkyl, aryl, arylalkyl, alkenyl and alkynyl; and wherein n and q may in each case independently of one another assume a value between 0 and 12, j and k may in each case independently of one another assume a value between 0 and 6, and p and m may in each case independently of one another assume a value between 0 and 12, with the following compounds being excluded:

N,N'-dimethyl-4,5,9,10-tetrahydro-2,7-diazapyreniumdiiodide;
1,1',2,2'-tetramethyl-4,4'-bispyridinium;
1,1',2-trimethyl-4,4'-bispyridinium;
N,N'-dimethyl-2,7-diazapyrenium;
N-methyl-N'-(p-toloyl)-2,7-diazapyrenium,
1,1'-dimethyl-2-phenyl-6-(p-toloyl)-4,4'-bispyridinium-diperchlorate;
1,1'-dimethyl-2-phenyl-4,4'-bispyridiumdiperchlorate;
6-(phenyl)-1,1',2-trimethyl-4,4'-bispyridiumdiperchlorate; and
1,1'-dimethyl-2-phenyl-6-(2,5-dichloro-3-thienyl)-4,4'-bispyridiumdiperchlorate.

20. Use of bispyridinium compounds having the general formula (I) as a functional unit in memory units.

21. Use of bispyridinium compounds having the general formula (Ib) as a functional unit in memory units.

22. The circuit element as claimed in claim 1, further comprising the bispyridinium molecules being two-aromatic-ring compounds with the general formula (I), Z$_a$ and Z$_b$ are selected from the group consisting of CH$_3$, —CH=CH$_2$, SH, —S—S—, —C(CO)CH$_3$, SiCl$_3$, Si(OR)$_3$, SiR(OR')(OR"), SiR(OR')$_2$, Si(R'R")NH$_2$, COOH, SO$_3$, PO$_3$H and NH$_2$, wherein R' and R" are selected from the group consisting of alkyl, aryl, arylalkyl, alkenyl or alkynyl; and wherein n and q may in each case independently of one another assume a value between 0 and 12, j and k may in each case independently of one another assume a value between 0 and 6, and p and m may in each case independently of one another assume a value between 0 and 12.

23. The circuit element as claimed in claim 22, in which the electrically inert molecules are compounds with a long-chain alkyl residue.

24. The circuit element as claimed in claim 23, in which the inert molecules have a head group by means of which they are covalently bonded to the first layer which is composed of the electrically insulating substrate material.

25. The circuit element as claimed in claim 24, in which the inert molecules are alkylsilyl compounds with the general formula

wherein in formula (II) p represents an integer between 1 and 30, and wherein R$_1$, R$_2$ and R$_3$ are selected from the group consisting of hydrogen, halogen, OR', NHR', and NR'R", and wherein R' and R" is equally alkyl.

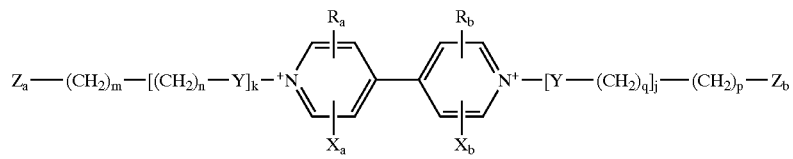

wherein in formula (I),
at least one of the carbon atoms of the two aromatic ring systems of the bispyridinium unit can be replaced independently of one another by at least one grouping X$_a$ and X$_b$ which in each case represents a heteroatom which is selecting from the group consisting of S, N, and O and a blank;
at least one of the carbon atoms of the two ring systems may, in each case independently of one another, have a substituent R$_a$ and R$_b$, wherein R$_a$ and R$_b$ may together form a bridge between the two aromatic ring systems, which bridge comprises 1 to 3 atoms, wherein the atoms are chosen independently of one another from C, S, N and O, and may be linked to one another by a single, double or triple bond and, furthermore, may have a substituent R$_c$, with the substituent R$_c$ having the meaning indicated above for R$_a$ and R$_b$;

Y is selected from the group consisting of CH$_2$, O, S, NH, NR', COO, CONH, CH=CH, C≡C and aryl;

26. The circuit element as claimed in claim 22, further comprising a plurality of discrete areas which are composed of the first electrically conductive material are embedded in the substrate material and are applied to the substrate material.

27. The circuit element as claimed in claim 22, in which the first electrically conductive material is selected from the group consisting of gold, silver palladium, platinum and silicon.

28. The circuit element as claimed in claim 22, in which the layer which is composed of the second electrically conductive material comprises titanium and aluminum.

29. The circuit element as claimed in claim 22, further comprising the first electrically conductive material and the second electrically conductive material being in the form of electrodes.

* * * * *

UNITED STATES PATENT AND TRADEMARK OFFICE
CERTIFICATE OF CORRECTION

PATENT NO. : 6,998,637 B2  
APPLICATION NO. : 10/600750  
DATED : February 14, 2006  
INVENTOR(S) : R. Johannes Luyken et al.

Page 1 of 1

It is certified that error appears in the above-identified patent and that said Letters Patent is hereby corrected as shown below:

On the Title page, field number (30) listed as Foreign Application Priority Data, delete " 102 27 850 " and add -- 102 27 850.4 --;

Title page 2, under the listing OTHER PUBLICATIONS, first column, line 11, delete " p. 597H " and add -- p. 597ff-- ;

Column 2, line 60, equation formula, delete " $\mathbf{bipy^{2+} + e^- \leftrightarrows bipy^+}$ " and add -- $bipy^{2+} + e^- \leftrightarrow bipy^+$ --.

Signed and Sealed this

Third Day of April, 2007

JON W. DUDAS  
*Director of the United States Patent and Trademark Office*